United States Patent
Prusiner et al.

(10) Patent No.: US 9,658,213 B2
(45) Date of Patent: May 23, 2017

(54) ISOTOPIC LABELING FOR THE MEASUREMENT OF GLOBAL PROTEIN LEVELS AND TURNOVER IN VIVO

(75) Inventors: Stanley B. Prusiner, San Francisco, CA (US); John C. Price, Hayward, CA (US); Sina Ghaemmaghami, San Francisco, CA (US); Al Burlingame, Sausalito, CA (US); Shenheng Guan, Palo Alto, CA (US)

(73) Assignee: The Regents of the University of California, Oakland, CA (US)

( * ) Notice: Subject to any disclaimer, the term of this patent is extended or adjusted under 35 U.S.C. 154(b) by 1033 days.

(21) Appl. No.: 13/704,498

(22) PCT Filed: Jun. 17, 2011

(86) PCT No.: PCT/US2011/040923
§ 371 (c)(1),
(2), (4) Date: Jul. 16, 2013

(87) PCT Pub. No.: WO2011/160045
PCT Pub. Date: Dec. 22, 2011

(65) Prior Publication Data
US 2014/0287957 A1    Sep. 25, 2014

Related U.S. Application Data

(60) Provisional application No. 61/356,540, filed on Jun. 18, 2010.

(51) Int. Cl.
*G01N 33/50* (2006.01)
*G01N 33/68* (2006.01)
*G01N 27/26* (2006.01)

(52) U.S. Cl.
CPC ..... *G01N 33/5088* (2013.01); *G01N 33/6842* (2013.01); *G01N 33/6848* (2013.01)

(58) Field of Classification Search
CPC .......... G01N 33/5088; G01N 33/6842; G01N 33/6848
See application file for complete search history.

(56) References Cited

U.S. PATENT DOCUMENTS

2002/0086288 A1    7/2002 Bird et al.
2005/0003375 A1    1/2005 Franza et al.
(Continued)

OTHER PUBLICATIONS

Doherty et al., "Turnover of the Human Proteome: Determination of Protein Intracellular Stability by Dynamic SILAC" Journal of Proteome Research (Jan. 2009) 8(1):104-112.
(Continued)

*Primary Examiner* — Jeremy C Flinders
(74) *Attorney, Agent, or Firm* — Karl Bozicevic; Bozicevic, Field & Francis LLP

(57) ABSTRACT

An entire complement or plurality of isotopically labeled amino acids are introduced into the diet of a test subject. Sufficient amounts of the isotopically labeled amino acids are provided to the subject in order to ensure that the subject incorporates a large percentage of isotopically labeled amino acids into newly synthesized proteins. Tissue samples are removed from the subject at different points in time and proteins are extracted and separated so that different proteins of different tissues can be individually analyzed and their amount and pattern of isotopic labeling can be determined. In a preferred embodiment, the methodology can be combined with proteolytic digestion to peptides and analysis by mass spectrometry in order to measure rates of protein turnover in vivo relating to thousands of different proteins.

17 Claims, 10 Drawing Sheets

(56) References Cited

U.S. PATENT DOCUMENTS

| | | |
|---|---|---|
| 2005/0238577 A1 | 10/2005 | Hellerstein |
| 2006/0020440 A1 | 1/2006 | Hellerstein |
| 2009/0171073 A1 | 7/2009 | Kobilka et al. |
| 2009/0240041 A1 | 9/2009 | Goodman et al. |
| 2010/0086480 A1 | 4/2010 | Williams |

OTHER PUBLICATIONS

Frank et al., "Stable Isotope Metabolic Labeling with a Novel 15N-Enriched Bacteria Diet for Improved Proteomic Analyses of Mouse Models for Psychopathologies" PLOS One (Nov. 13, 2009) 4(11):e7821.

Krijgsveld et al., "Metabolic labeling of C. elegans and D. melanogaster for quantitative proteomics" Nature Biotechnology (Aug. 2003) 21(8):927-931.

McClatchy et al., "15N Metabolic Labeling of Mammalian Tissue with Slow Protein Turnover" Journal of Proteome Research (May 2007) 6(5):2005-2010.

Wu et al., "Metabolic Labeling of Mammalian Organisms with Stable Isotopes for Quantitative Proteomic Analysis" Anal. Chem. (Sep. 2004) 76(17):4951-4959.

ISOTOPIC LABELING FOR THE MEASUREMENT OF GLOBAL PROTEIN LEVELS AND TURNOVER IN VIVO

CROSS-REFERENCE

This application is a 371 National Phase of International Patent Application Serial No. PCT/US2011/040923, filed Jun. 17, 2011 which claims priority to U.S. Provisional Patent Application Ser. No. 61/356,540, filed Jun. 18, 2010, which are incorporated herein by reference in their entirety noting that the current application controls to the extent there is any contradiction with any earlier applications and to which applications we claim priority under 35 USC §120.

FIELD OF THE INVENTION

The invention relates generally to the field of assay technology, and more particularly to a method of measuring changes including protein turnover in vivo using isotopically labeled amino acids.

BACKGROUND OF THE INVENTION

Several methods exist for system-wide measurement of protein concentrations. In one approach, antibody arrays are used to specifically bind to multiple proteins in complex mixtures. However, optimal binding between protein antigens and antibodies tend to vary widely, making the approach generally unsuitable for proteome-wide analysis. A second method involves the use of heavy isotope standards. The standards are mixed with the protein samples to provide an internal reference for the measurement of protein concentration. These methodologies measure steady-state protein levels and cannot analyze the dynamics of in vivo proteome turnover.

Protein molecules are in dynamic equilibrium in vivo: they are continuously synthesized and degraded during the lifetime of the organism (1, 2). The turnover rate of proteins can vary from minutes to years, often conforming to their biological functions (3, 4). The constant renewal of the protein population is an energy-intensive process, yet it allows the cell to rapidly modulate protein levels in response to changes in the environment (5, 6). Proper proteome dynamics are critical to normal development and maintenance of health (7, 8). For example, the dysregulation of protein turnover has been implicated in the aging process (9), increased degradation of the CTFR chloride channel is a primary cause of cystic fibrosis (10), and the inability to clear protein aggregates leads to pathogenic accumulations in Alzheimer's, Parkinson's, Creutzfeldt-Jakob, and other age-related diseases (11).

The turnover rate of a protein is established by its relative rates of synthesis and catabolism. Thus, the lifetime of a protein is influenced by a number of regulated processes at the level of the cell (transcription, translation, proteolysis, autophagy) and tissue (development and regeneration) as well as its biochemical properties (structural stability, hydrophobicity, sequence motifs) (1, 12-15). The ability to measure turnover rates on a proteome-wide scale can help elucidate the interplay between these factors and identify novel processes that play a role in proteome homeostasis. It can also identify proteins whose dysregulation influences or results from pathological processes.

Traditionally, protein turnover has been studied by measuring the incorporation of radioactive, tracer amino acids into proteins or bulk tissues (16-20). The advent of modern proteomics has enabled scientists to utilize mass spectrometry to detect the incorporation of stable isotopes into proteins (21, 22).

SUMMARY OF THE INVENTION

Measuring the dynamics of protein turnover in vivo using isotopically labeled amino acids is disclosed. In vivo protein concentrations are maintained through dynamic control of protein synthesis and degradation. These global dynamics are known to be effected by a number of disorders and bioactive drugs. The invention provides for in vivo analysis of protein dynamics for applications in the diagnosis, treatment and management of diseases, including but not limited to identifying novel targets for therapeutics, and elucidating the mechanism of drug toxicities.

Advances in systems biology have allowed for global analyses of mRNA and protein expression, but large-scale studies of protein dynamics and turnover have not been conducted in vivo. Protein turnover is an important metabolic and regulatory mechanism in establishing proteome homeostasis, impacting many physiological and pathological processes. The present invention uses organism-wide isotopic labeling to measure the turnover rates of ~2,500 proteins in multiple mouse tissues. Although the brain is often a difficult target for in vivo studies, the invention measures turnover rates spanning four orders of magnitude. Through comparison of the brain with the liver and blood, the invention shows that within the respective tissues, proteins performing similar functions often have similar turnover rates. Proteins in the brain have significantly slower turnover (average lifetime of 9.0 d) compared to those of the liver (3.0 d) and blood (3.5 d). Within some organelles (such as mitochondria), proteins have a narrow range of lifetimes, suggesting a synchronized turnover mechanism. Protein subunits within complexes of variable composition have a wide range of lifetimes, whereas those within well-defined complexes turnover in a coordinated manner. Together, the data represent the most comprehensive in vivo analysis of mammalian proteome turnover to date. The invention is useful in accessing in vivo proteome homeostasis in any model organism that will tolerate a labeled diet including the analysis of neurodegenerative diseases in vivo.

The invention includes a method of testing effects of a drug on protein turnover, by first feeding a group of substantially identical test animals such as mice a composition comprised of a plurality of isotopically labeled amino acids. The composition may include two or more different labeled amino acids which can include five or more, or all naturally occurring amino acids. After feeding the composition to the test animals the test animals are divided into a first group and a second group. A drug is administered to a first group while no drug is administered to a second group. The labeled amino acids are allowed to incorporate into proteins in the animals in the first group and in the second group. Thereafter, tissue samples may be harvested from animals of the first group and the second group at any desired period of time such as one day, two days, three days or more. The sampling may be hourly, daily, or every other day or more. Further, the sampling may be from a single type of tissue of the animals within the first and group and the second group or may be of two or more, three or more, four or more, five or more, different types of tissue within the animals of each group. After analyzing the tissue samples from the two groups of animals the level of isotope in the samples from the first group is compared with the level or isotopes in the samples from the second group of animals. This comparison makes it possible to determine effects on protein turnover caused by the drug administered to the first group of test animals.

When the analyzing is carried out it can be carried out relative to a single protein, meaning multiple copies of the same amino acid sequence. However, the invention is applicable to carrying out the analysis with respect to multiple different proteins, meaning multiple copies of proteins with different amino acid sequences. The invention may be applied to a plurality of different proteins, meaning applied to a plurality of molecules which are different from each other in their amino acid sequence and/or confirmation. The invention may be applied to 2 or more different proteins, 10 or more different proteins, 50 or more different proteins, 100 or more different proteins, 1,000 or more different proteins. Further, those different proteins may be tracked within a single tissue or a plurality of different tissues. The analysis of the proteins may be tracked in 2 or more different tissues, 5 or more different tissues or any number of different tissues within the animals. The subjects fed a formulation of the invention can be any plant or animal, but is generally a multicellular animal and is generally an animal typically used in a test environment such as a multicellular mammal such as mice which may be genetically engineered or specifically bred mice.

The analyzing of harvested tissue samples can be carried out in order to determine a level of isotope present. An aspect of the invention involves determining the level of isotope present within multiple different tissues.

Another aspect of the invention involves determining the level of multiple different proteins and multiple different tissues based on a single administration of a composition of the invention to the subject. Thus, for example, the ratio of labeled amino acids appearing within proteins in different tissues can be determined with respect to one tissue to another tissue. Further, the ratio of the same protein in one tissue relative to another tissue can be determined Information obtained as a result of the analysis can be used to determine the effects of drugs on protein turnover in different types of tissues and more specifically turnover of different types of proteins in different types of tissues.

An aspect of the invention is that the methodology is applicable to any organism which can be fed a diet consisting of isotopically labeled amino acids.

Another aspect of the invention is that the method can be used on animals which serve as disease models including transgenic mice.

Another aspect of the invention is that it may be used with mass spectroscopy and provide detailed information regarding rates of protein turnover, for individual proteins or small numbers of selected proteins, as well as for very large numbers of proteins concurrently.

Yet another aspect of the invention is that the proteins analyzed can be proteins in any type of tissue including brain, liver, blood muscle, heart, stomach, spleen, lung and bone.

An aspect of the invention is that a large number of proteins can be simultaneously analyzed within a biological sample.

Another aspect of the invention is that labeling can be conducted with fully (100%) labeled amino acids. Therefore, turnover rates can be assessed by the single-step kinetics of amino acid incorporation without conducting complex pulse-chase analyses.

Another aspect of the invention is that although tracer methods can only measure the total incorporation of label, mass spectrometry can analyze the population distribution of partially labeled species for a given protein. Thus, turnover rates can be measured in instances in which upstream processes, such as label uptake into tissue, are rate-limiting.

Recent studies have shown that rats can be isotopically labeled using a diet source supplemented with $^{15}N$-enriched, blue-green algae (*Spirulina platensis*) (23). The present invention uses a similar approach to measure the in vivo turnover kinetics of proteins in the brains of wild-type, inbred mice (FVB) and provide a comparison of these dynamics to the blood and liver proteomes.

An aspect of the invention is a method of testing drugs to determine the effect of the drugs on proteins in an animal such as a human. The method can be a method whereby a standard can be provided for use by governmental drug approval agencies such as the FDA to determine the effect of drugs on the proteome of any animal and in particular a human. The method may include a method of testing effects of a drug on protein turnover, comprising the steps of:

feeding a group of substantially identical test animals a composition of 15N-enriched blue-green algae (*Spirulina plantenis*) comprised of a plurality of isotopically labeled amino acids;

dividing the test animals into a first group and a second group:

administering a drug to the first group, while not administering the drug to the second group;

allowing the labeled amino acids to incorporate into proteins of the animals in the first group and the second group;

harvesting tissue samples from animals of the first group and the second group;

analyzing tissue samples from the first group and the second group and determining a level of isotope in the tissue samples; and comparing the level of isotope in the samples from the first group with the level of isotope in the samples of the second group in order to determine an affect on protein turnover caused by the drug;

wherein the first group of test animals and the second group of test animals each comprise two or more animals, and further wherein tissue is harvested from each group of animals at two or more different points in time;

Wherein the analyzing comprises:

separating proteins based on protein size or other physical characteristic, such including but not limited to isoelectric point; and subjecting proteins of a given size to mass spectrometry for determination of the amount and pattern of isotopic labeling in said proteins;

wherein the proteins isolated are subjected to partial proteolytic degradation, with an enzyme such as trypsin; and peptide fragments of said proteolytic digestion are subjected to mass spectrometry for determination of the amount and pattern of isotopic labeling in said peptides.

These and other objects, advantages, and features of the invention will become apparent to those persons skilled in the art upon reading the details of the method as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 1B schematically shows the incorporation of the $^{15}N$ into amino acids. FIG. 1C shows nine schematic spectrographs of $^{15}N$ incorporation over time.

FIG. 5A shows an average labeled population curve for blood-extracted serum albumin Symbols represent median values for 62 detected peptides. Black arrow bars represent the standard deviation between peptides. Lighter bars represent SEM. FIG. 5B shows the global analysis of variance in turnover of peptides belonging to the same protein. The box shows the medium interquartile range (IQR) of the coefficient variations (CV) of turnover rates of peptides encompassing a single protein, for all protein analysis of the three tissues.

FIG. 9A in cases for which only a single probe within a protein can be labeled (top row). The kinetics of labeled population may reflect the turnover rate or the availability of $^{15}N$ in the amino acid pool. If more than one probe exists these two parameters can be deconvoluted by analyzing the mass distribution of the labeled population. In FIG. 9B the frequency at which each amino acid appears in the tryptic peptides analyzed in this study. Most peptides contain fewer than two of any given amino acid, making the above deconvolution difficult in SILAC labeling experiments using a single labeled amino acid. Lysine and arginine (designated by the stars) are two commonly used probes in SILAC analysis.

DETAILED DESCRIPTION OF THE INVENTION

Before the present assay methodology and method of using same to identify targets for therapeutics are described, it is to be understood that this invention is not limited to particular assays and methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a label" includes a plurality of such labels and reference to "the animal subject" includes reference to one or more animals of the type mentioned and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

INVENTION IN GENERAL

Figure 1:
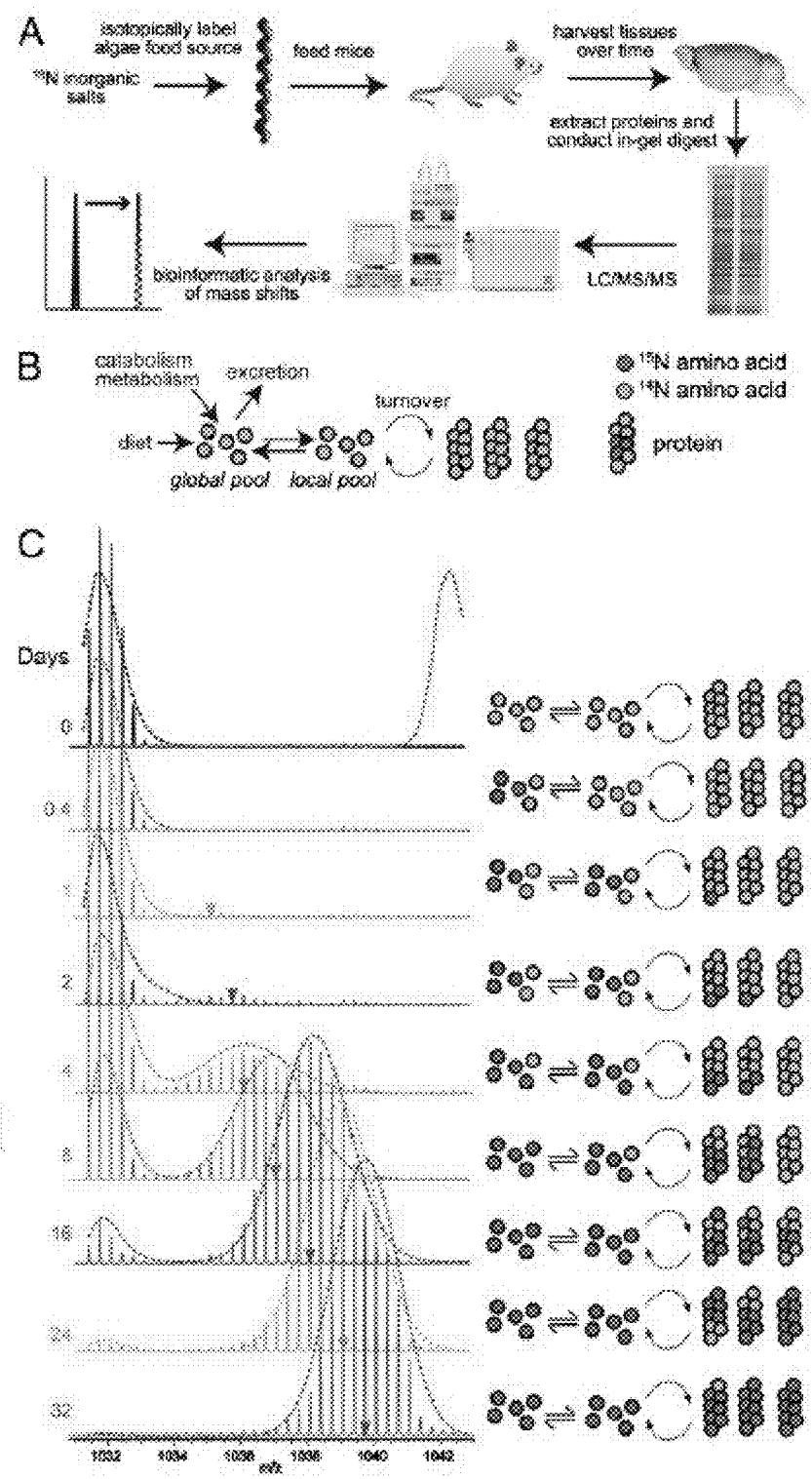
FIG. 1 includes 1A, 1B and 1C wherein 1A is a flow diagram showing steps that may be taken in accordance with the present invention in order to include an isotopically labeled amino acid into a subject followed by harvesting and analyzing tissue from the subject.

The method consists of introducing the entire complement of isotopically labeled amino acids in the diet of an organism as shown in the flow diagram of FIG. 1. Said isotopically labeled amino acids could contain stable isotopes of their component chemical constituents including but not limited to $^{15}N$, $^{13}C$, $^{2}H$, or $^{18}O$. In some embodiments, saturating concentrations of said isotopically labeled amino acids are fed to the test subject such as the mouse shown in FIG. 1. Feeding continues over a period of time sufficient to ensure that the metabolism of the organism (shown as a mouse in FIG. 1, but could be another living organism, including a human) will incorporate a maximal percentage of the isotopic label (e.g. $^{15}N$) into newly synthesized proteins. Alternatively, less than saturating concentrations of isotopically labeled amino acids are feed to the test subject, but the concentrations fed are sufficient to incorporate enough of the isotopic label (e.g. $^{15}N$) into newly synthesized proteins to allow measurement by mass spectrometry or other methods known in the art. The saturation level may be 25%, 50%, 75%, 90%, 99% or more of all proteins in the subject. Tissue samples are harvested at different points in time which could be any interval including every 24, 48, 72, 96 hours. By analyzing the tissue samples taken at different times the isotope incorporation into any protein within the organism is determined.

The test subject can be any animal, including but not limited to, a human, mouse, rat, monkey, cow, hog, sheep, horse, dog, or cat.

Figure 2A:
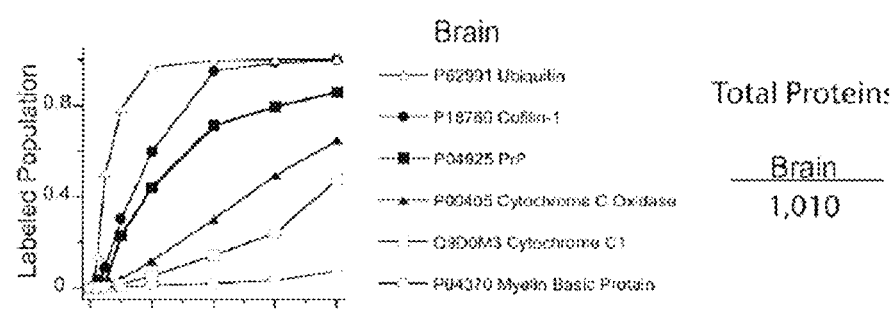
FIG. 2 includes a graph 2A which shows an analysis of brain tissue, a graph 2B which shows an analysis of liver tissue, and a graph 2C which includes an analysis of blood tissue.
Figure 2B:
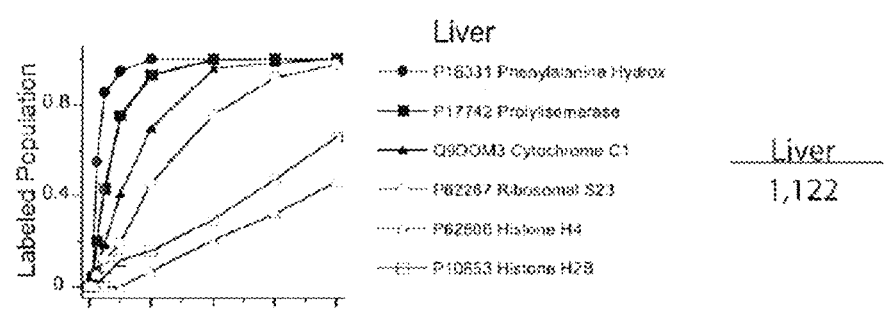
Figure 2C:
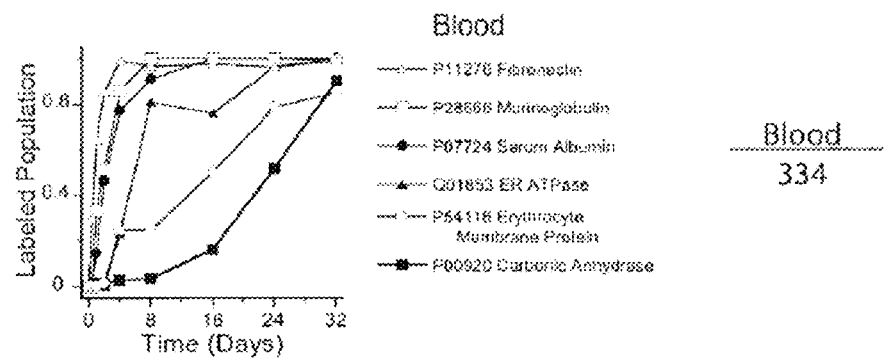
Figure 3:
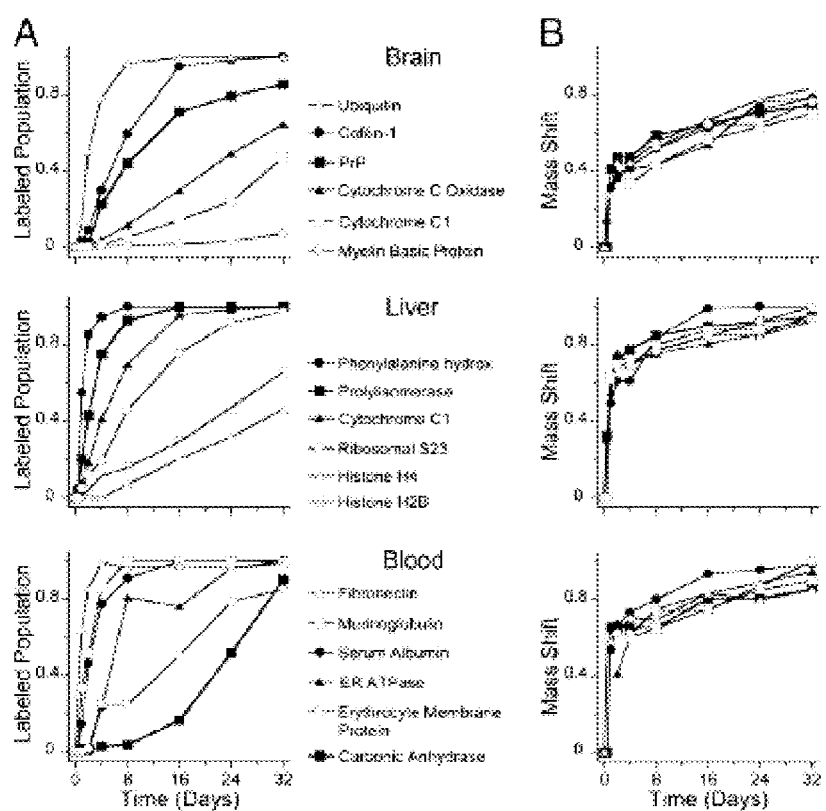
FIG. 3 includes three graphs on the left 3A and three graphs on the right 3B. These graphs show the kinetics of peptide-labeled populations and mass shifts. Measurements (symbols) were made for individual peptides from the designated protein extracted from the brain, liver and blood.

Examples of three different types of samples taken from mice are shown in FIGS. 2A, 2B and 2C. Proteins are entracted from the samples and a gel is used to carry out protein separation. Coupling this labeling methodology with mass spectroscopy, the rates of protein turnover in vivo are measured. The turnover rates of ~2,500 proteins in the brain (2A), liver (2B) and blood (2C) can be measured and those skilled in the art, reading this disclosure will understand how the technique can measure protein turnover rates for more than 20,000 different proteins. In various embodiments, the methods of the present invention can measure 1, 2, 3, 4, 5, 10, 50, 100, 1000, 2000, 5000, 10000, 20000 or more proteins from a single sample. This methodology can be used in any organism and used with an in vivo disease model such as a transgenic mouse.

The invention is useful in measuring the effects of a bioactive drug on proteome dynamics. Comparing the rates of protein turnover prior and subsequent to administration makes it possible to determine the targeted and toxic effects of a therapeutic.

The method can also be used to identify novel drug targets. Analysis of proteome dynamics in disease models makes it possible to identify proteins whose dysregulation results in or is caused by disease. As such, the technique disclosed here provides a robust methodology for studying alterations in proteome dynamics that feature in many diseases, including neurodegenerative disorders.

The method can be used for monitoring disease activity, severity or prognosis, or for the management of patients with diseases. Analysis of proteome dynamics in patients with disease can provide metrics or biomarkers for evaluation, treatment and medical management.

Current proteomic technologies can only measure steady-state protein concentrations and are not capable of measuring protein dynamics. The importance of dynamics is critical in the investigation of development and disease (Hellerstein, M. K. (2004) New stable isotope-mass spectrometric techniques for measuring fluxes through intact metabolic pathways in mammalian systems: introduction of moving pictures into functional genomics and biochemical phenotyping, *Metab. Eng.* 6, 85-100).

Most previous methods for measurement of protein turnover could only measure individual proteins after extensive purification of the target protein (Nikolov, E. N., Dineva, B. B., Dabeva, M. D., and Nikolov, T. K. (1987) Turnover of ribosomal proteins in regenerating rat liver after partial hepatectomy, *Int. J. Biochem.* 19, 159-163; Verzijl, N., DeGroot, J., Thorpe, S. R., Bank, R. A., Shaw, J. N., Lyons, T. J., Bijlsma, J. W., Lafeber, F. P., Baynes, J. W., and TeKoppele, J. M. (2000) Effect of collagen turnover on the accumulation of advanced glycation end products, *J. Biol. Chem.* 275, 39027-39031). Previously disclosed methods for measuring the turnover of large numbers of proteins concurrently have been based on administration of single amino acid labels (e.g., $^{15}N$-lysine, $^{13}C$-leucine, $^{2}H$-leucine). These methods all have technical limitations that reduce the sensitivity and precision of measured turnover rates compared to the method disclosed herein, due in part to the much lower degree of isotopic labeling achieved with previous methods. Without being bound by theory, because the isotopic labeling achieved with individual labeled amino acids in a protein or in a peptide derived from a protein is so much less extensive than that achieved when all amino acids are isotopically labeled, the discrimination between newly synthesized ("labeled") proteins and previously present ("unlabeled") proteins is much more difficult with previous methods.

The methodology disclosed and described here allows the turnover of thousands of individual proteins to be measured simultaneously without purification of individual proteins. The measurement of proteome dynamics during drug administration will allow the effects of the drug on the proteome to be evaluated. Administration of a drug may not perturb the overall concentration of its target protein due to compensatory changes in synthesis or degradation. Therefore, current methods of monitoring protein concentration cannot assess drug effects on proteome homeostasis.

A second important feature of the methodology disclosed and described here is that it can be conducted in live animals. Previously, many measurements of protein dynamics for hundreds of proteins have been conducted in cell culture. However, the methodology of the present invention extends this approach to complex organisms and more relevant disease models.

In order to carry out a particular embodiment of a method of the invention $^{15}N$ inorganic salts are used to make broth for cultures of *Spirulina*. Dried $^{15}N$-labeled algae is used to supply protein in a mouse diet as is shown in the flow diagram of FIG. 1.

In various embodiments, one or more isotopic labels can be used, including, but not limited to $^{15}N$, $^{13}C$, $^{2}H$, or $^{18}O$. In some embodiments, the isotopic labels can be incorporated with one or more different amino acids to create different isotopically labeled compositions.

In some embodiments, the isotopically labeled compositions can be ingested, such as consumed in a solid or liquid form, injected or infused into the test subject. In other embodiments, the isotopically labeled compositions can be delivered via an implantable device. In various embodiments, one or more isotopically labeled compositions can be delivered simultaneously or sequentially, and can be delivered via one or more of the routes of delivery previously described (ingestion, infusion, etc.).

In some embodiments, isotopically labeled compositions can be delivered to the test subject in a known amount. In some instances, this can be useful for quantifying amounts of isotopic label in a sample taken from a test subject. In some instances, the amount of isotopic label does not need to be known, such as where analysis of relative amounts, or presence vs. absence of isotopic label is measured.

At designated points in time samples are taken as indicated in the "harvest tissues over time" step shown in FIG. 1. The tissue samples can be taken at any time and a convenient time is once every four days. The tissue samples removed are homogenized and fractionated according to molecular weight in a 1D SDS-PAGE gel. In-gel digests liberate peptides from the gel. The liberated peptides are then analyzed by LC/MS/MS.

The change in molecular weight and the relative populations of labeled peptides are compared in a proteome-wide bioinformatic analyses. The data obtained from the analysis relating to newly synthesized proteins is measured and the results are shown in FIGS. 2A, 2B and 2C for individual proteins for each of the brain (2A), liver (2B), and blood (2C). For each of the types of tissue specific proteins are listed. Further, on the far right of FIGS. 2A, 2B and 2C the total number of proteins are shown.

Testing Effects of Drug on Protein Turnover

The assay methodology of the invention can be used in a method of testing the effects of a drug on protein turnover. The method is carried out by feeding a group of substantially identical test animals a composition comprised of a plurality of an isotopically labeled amino acids. As shown in FIG. 1 the animals may be fed an isotopically labeled algae food source which comprises organic salts and a $^{15}N$ label. The animals are fed a sufficient amount of the food in order to provide for a saturating concentration of amino acids to ensure that the metabolism of the organism will incorporate a maximal percentage of the isotopic label into newly synthesized protein. The animals within the group are all substantially identical and may be transgenic animals such as transgenic mice.

The test animals are divided into a first group and a second group. A pharmaceutically active drug to be tested is administered to the first group and no drug is administered to the second group. The drug may be administered prior to, during or after the feeding. In one embodiment the drug is administered as the feeding with the isotopically labeled food begins.

Sufficient time is allowed to pass so that the isotopic label incorporates into proteins of the animals in both the first group and the second group. This period of time can vary from hours to days to weeks or more. It in general, the feeding will continue over a period of days. During this time, tissue samples can be harvested from the animals. In one embodiment all of the tissue samples are taken from all of the animals at substantially the same time. The harvesting is them repeated two or more times with the harvesting occurring with all of the animals during substantially the same time period.

After the tissue samples are harvested, they may, if necessary, be homogenized and subjected to analysis. The analysis includes determining the level of isotope present in the sample tissues in both the first group of test animals and the second group of test animals. The analysis is carried out in order to determine a level of the isotope present in the samples. The samples may be from a single type of tissue of each of the animals or may be from several different types of tissue.

Once the analysis is complete and the level of the isotope in a particular tissue type has been determined the isotope level measured in the first group of animals is compared with the isotope level in the second group of animals. This comparison makes it possible to determine the effect, if any, on protein turnover caused by the test drug and that effect can be seen in specific proteins of the tissue.

DEFINITIONS

The term "proteome" refers to an entire set of proteins expressed by a genome, cell, tissue or organism. The proteome is the set of expressed proteins in a given type of cell or an organism at a given time under defined conditions. Those skilled in the art will understand that the proteome for the cells of a particular type of tissue will differ from the proteome of the cells of a different type of tissue from the same organism. Those skilled in the art will also understand that the proteome will be larger than the genome, especially in eukaryotic organisms indicating that there are more proteins then there are genes in the organism. This is due to alternative splicing of the genes and post-translational modifications such as glycosylation and phosphorylation.

Those skilled in the art will understand that the proteome has at least two levels of complexity which are lacking in the genome. When the genome is defined the sequence of nucleotides, the proteome cannot be limited to the sum of sequences of the proteins present. The knowledge of the proteome requires a knowledge of (1) the structure of the proteins in the proteome and (2) the functional interaction between the proteins.

The term "isotopic labeling" refers to any technique for tracking the passage of a sample substance through a system. Substances labeled by incorporating an isotope into its chemical composition. The isotope may be $^{15}N$ or other isotope used by those skilled in the art, e.g. $^{13}C$, $^{14}C$, $^{40}K$ and hydrogen isotopes as well as combinations thereof. The labeled isotope may be detected in at least two different ways. Isotopes have different masses. Accordingly, the presence of the different isotopes, particularly those termed stable isotopes by those familiar with the art, within a composition can be separated using mass spectrometry. The molecules containing the isotopes also have different vibrational modes from those not containing the isotope. Thus, these different vibrational modes can be detected using infrared spectroscopy. Other features of stable isotopes (such as magnetic spin) can be detected by methods known in the art (e.g., by nuclear magnetic resonance).

Data Analysis

The data provided show bursts in mass shifts, indicating rapid increases in $^{15}N$-labeled amino acids in the local pool from the dietary algae. The initial increase was lower in brain than in liver and blood, reflecting the trafficking of dietary amino acids. The $^{15}N$-labeled amino acids enter the blood and traverse multiple tissues, including the gut and liver, before they reach the brain. The sequential flux through multiple tissues enables the introduction of $^{14}N$-labeled amino acids (through local metabolic and catabolic processes) prior to flow into the local brain pool. Thus, in the brain the initial burst of $^{15}N$ labeling of the local brain pool is reduced in comparison to upstream tissues. The second, slower phase of the mass shift corresponds to the "recycling" of amino acids through catabolic and metabolic processes. In other words, the breakdown of internal proteins constantly dilutes the dietary supply of $^{15}N$-labeled amino acids. Before complete labeling of the amino acid pool can be achieved, the internal pool of $^{14}N$-containing proteins needs to be completely depleted. In the brain, the prolonged recycling phase is slower in comparison to the liver and blood. This result is expected given that brain proteins are relatively long-lived in comparison to liver and blood proteins, leading to an extended recycling phase. Future analysis of the free amino acid enrichment kinetics in these various tissues could be used to refine this model.

Steady-state protein levels, in themselves, are not predictive of turnover rates. Whereas the static level of a protein is established by the relative ratio of synthesis and degradation rates, its lifetime is determined by the magnitude of these rates. This idea is supported by our data. In proteomic analyses of tryptic peptides, the relative steady-state level of a protein can be crudely estimated by the ratio of observable peptides to the theoretical number of peptides expected from that protein [Protein Abundance Index (PAI)] (37). Within our data, there is no significant correlation between turnover rates and PAI (FIGS. 10A and 10B), suggesting that proteins with similar abundances can have a wide range of turnover rates.

Our data suggest that protein turnover is regulated at the level of the tissue, organelle, and protein complex. The rate of turnover is generally slower in the brain compared to the blood and the liver. The relatively slow rate of bulk protein turnover in the brain had been previously observed (18, 21). We show that this is not only due the presence of stable proteins that are uniquely expressed the brain, but also because proteins that are shared between the three tissues have a longer half-life in the brain—by a factor of 2 to 5. It is interesting to note that in rats, the organ-specific metabolic rate per gram of liver has been estimated to be 5 times greater than the equivalent mass of brain (38). The observation suggests that the difference in the metabolic rate of these two tissues may be largely due to differences in energy commitment to proteome turnover.

Figure 7:
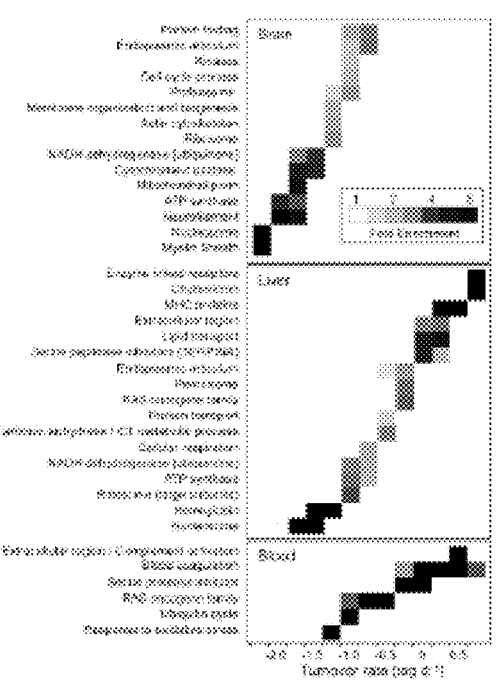
FIG. 7 shows the correlation between function and turnover rates. The functional categories based on the gene ontology (GO) database were clustered into the categories listed along the Y axis. The turnover rates for the proteins belonging to the GO clusters were enriched (shown by gray scaling) with high statistical significance (P<0.001) for the indicated rate bin.

We observe statistically significant similarities within turnover rates of proteins localized to specific organelles. Mitochondrial proteins, whether encoded by mitochondrial or nuclear DNA, have similar turnover rates as shown in FIG. 7. Mitochondrial and nuclear proteins tend to have longer half-lives than cytosolic proteins, which in turn, are more stable than proteins of the endoplasmic reticulum. For some organelles, this coordinated turnover may reflect autophagy as a primary route of degradation. The turnover of mitochondria as a unit through autophagy (mitophagy) is known to be a primary method for mitochondrial regulation in the cell (39, 40). Mitochondrial protein lifetimes vary between the liver and the brain, suggestive of different tissue-specific mitophagy rates.

For many protein complexes, turnover rates of constituent subunits fall within a small range. The 20S proteasome core complex in the brain and liver has a narrow range of turnover rates. Although it has been suggested that multiple 20S subtypes are present in cells and tissues (41), our data suggest that alternative proteasome compositions are either rare or have the same lifetime as the canonical core complex. Synthesis of abundant multiprotein complexes, such as the ribosome and the proteasome, represent a considerable energy investment for the cell. The coordinated turnover of these complexes may represent an energy-conservation strategy by the cell to avoid the presence of orphan subunits. For example, the regulation of turnover among protein and RNA ribosomal subunits had been previously established (20). For a few complexes, such as the Cop9 signalosome complex (CNS), we observed a broad range of turnover rates. CNS is a regulated component of the ubiquitine-proteasome degradation pathway associated with specific developmental processes (42). Distinct CNS populations with varying subunit compositions and activities have been identified (43). Consistent with these observations, our data suggest the presence of multiple CNS populations with distinct half-lives.

Figure 10:
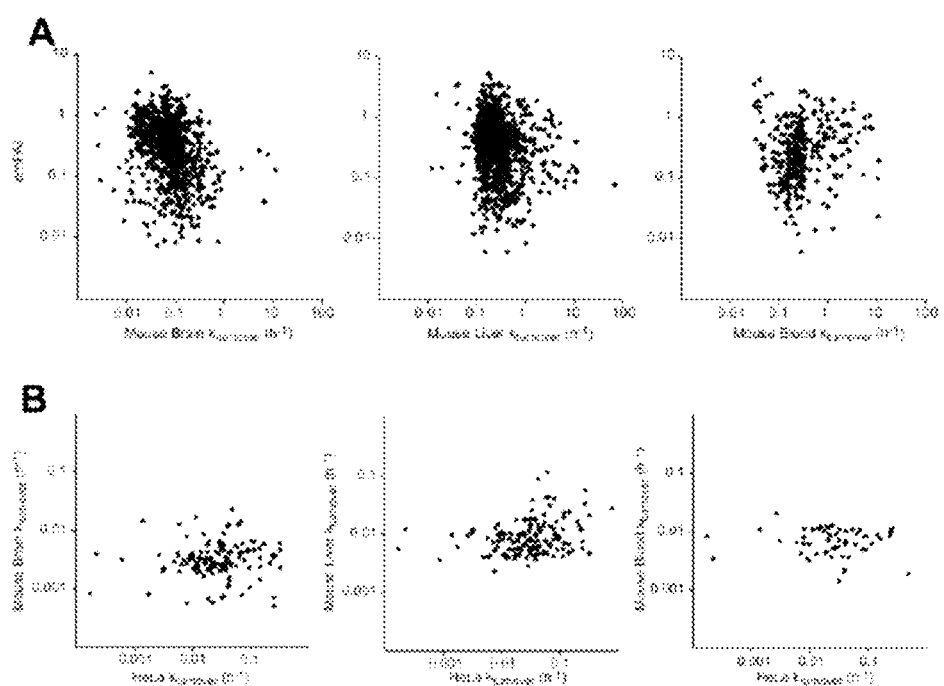
FIG. 10 includes the three graphs of 10A and three graphs of 10B. Correlating turnover rates in mice to protein levels (10A) and turnover rates to cell culture (10B) is shown.

A recent analysis of cultured HeLa cells succeeded in measuring the turnover rate of ~600 proteins (22). Of these, we found ~150 homologous mouse proteins in our in vivo dataset for at least one tissue. A comparison of the data reveals little correlation between turnover rates in culture with turnover rates in mice (FIG. 10B). Indeed, the turnover rates measured in culture were significantly faster than the in vivo measurements. This variability may be due to the continuously proliferating nature of transformed cell lines. Unlike differentiated cells, a dividing cell line is in continuous need of protein production to supply newly generated daughter cells. The regeneration of liver mass that occurs through the proliferation of hepatic cells was shown to reduce apparent protein half-life (20). Additionally, the range of half-lives in HeLa cells appears to be much broader than the corresponding measurements in vivo, perhaps because some of the mechanisms that regulate protein turnover in vivo (e.g., autophagy, tissue regeneration) are absent in culture. These results highlight the limitations of cultured cell lines as models of in vivo proteome homeostasis.

Future kinetic analysis of low abundance proteins can be performed by fractionating tissue homogenates using established purification techniques. Future studies that combine protein turnover measurements with quantitative proteomic strategies will allow the absolute protein degradation rates to be established on a proteome-wide scale. This work provides the methodology and theoretical framework necessary to conduct proteome-wide analyses of in vivo protein turnover in any model organism and environmental condition where a labeled diet can be incorporated into the experimental design. The approach will be generally useful in analyzing relationships between proteome homeostasis and biological phenotypes of interest, particularly in the brain, where protein turnover is critical to normal function (32, 33) and accumulation of misfolded protein aggregates is a primary characteristic of neurodegenerative disease (44, 45).

Spectrometry

The sequence of the isolated peptides and the identification of proteins can be determined by a combination of tandem mass spectrometry and computer-assisted database search programs, such as MASCOT (Matrix Science Ltd, UK) (Perkins, D N, et al. (1999) "Probability-based protein identification by searching sequence databases using mass spectrometry data" Electrophoresis 20, 3551-3567) or SEQUEST (Trademark, University of Washington, Seattle Wash.) (McCormack, A. L. et al. (1996) "Direct Analysis and Identification of Proteins in Mixtures by LC/MS/MS and Database Searching at the Low-Femtomole Level", Anal. Chem. 69, 767-776; Eng, J. K. et al. (1994) "An Approach to Correlate Tandem Mass Spectral Data of Peptides with Amino Acid Sequences in a Protein Database" J. Amer. Soc. Mass. Spectrom., 5, 976-989; U.S. Pat. No. 5,538,897 (Jul. 23, 1996) Yates, III et al.). Both, MASCOT and SEQUEST takes all known genomic sequence, computes all possible theoretical CID spectra and compares them to experimental CID spectra for matches and sequence identification, all of which are incorporated herein by reference.

The following references relate to the application of mass spectrometric techniques to protein identification, particularly those related to proteome analysis: Ideker T, Thorsson V, Ranish J A, Christmas R, Buhler J, Eng J K, Bungarner R, Goodlett D R, Aebersold R, Hood L "Integrated genomic and proteomic analyses of a systematically perturbed metabolic network." Science. May 4, 2001; 292(5518):929-34; Gygi S P, Aebersold R. "Mass spectrometry and proteomics." Curr Opin Chem Biol. October 2000; 4(5):489-94.; Gygi S P, Rist B, Aebersold R "Measuring gene expression by quantitative proteome analysis" Curr Opin Biotechnol." August 2000; 1 1(4):396-401; Goodlett D R, Bruce J E, Anderson G A, Rist B, Pasa-Tolic L, Fiehn O, Smith R D, Aebersold R. "Protein identification with a single accurate mass of a cysteine-containing peptide and constrained database searching." Anal Chem. Mar. 15, 2000; 72(6):1112-8.; and Goodlett D R, Aebersold R, Watts J D. "Quantitative in vitro kinase reaction as a guide for phosphoprotein analysis by mass spectrometry." Rapid Commun Mass Spectrom. 2000; 14(5):344-8; Zhou, H. et al (April 2001) Nature Biotechnol. 19:375-378, all of which are incorporated herein by reference.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Large-Scale Production of Ubiquitously $^{15}$N-Labeled Algae

In order to obtain the algae necessary for long-term labeling studies, we constructed a closed-loop bioreactor based on a bubble-lift circulator. Using $^{15}$N-enriched $NaNO_3$ as the sole nitrogen source, we produced near-uniform $^{15}$N-labeled Spirulina at a yield of 3 g of algae per L of broth. Mass spectral analysis of the Spirulina indicated that the final isotopic enrichment was >99.5% $^{15}$N. The labeled feed required for the entirety of our studies was supplied by ~60 L of Spirulina culture.

Algal Peptides and Peptide-Specific Relative Isotopic Intensities

Maximum isotopic enrichment of the algal diet was determined using peptides from four highly abundant Spir-ulina proteins. Isotopic enrichments of identical peptides from natural (t=0) and $^{15}$N-enriched (t=infinity) Spirulina protein were compared. Peptide-specific information was obtained including the Uniprot-listed name, accession number, and molecular weight (MW) of the protein. The peptide specific mass/charge (m/z), the charge state (z), and the amino acid sequence were determined. The expectation value obtained was the probability assigned by the Protein Prospector search engine that the peptide sequence could be assigned randomly. For each peptide, the time-point $^{15}$N incorporation measurement of unenriched (t=0) and $^{15}$N-enriched (t=inf) Spirulina were obtained.

Maintaining Mice on Algae Diet

Mice fed a diet based on Spirulina had no subchronic toxicities after 13 weeks of continuous feeding (24). Our diet formulation was similar to published protocols (21, 23). Mice were examined daily for general health and at least twice a week for body mass. Body mass fluctuated daily, but no mice lost or gained a significant fraction (>20%) of their pre-algae-diet body mass.

Peptide Identification

The computational analysis of the data was conducted utilizing computer scripts. All processed data, including the peptides, proteins, and their measured kinetic parameters.

Relative Isotopic Intensities for Detected Peptides and Proteins

Each of the peptides and proteins monitored throughout the labeling time-course were categorized according tissue (brain, liver, blood).

For the peptides, the Uniprot-listed name, accession number, molecular weight (MW), mass/charge (m/z), charge state (z), and amino acid sequence were assigned. The fraction file name was given to indicate the raw data file wherein the peptide can be found at the listed liquid chromatography (LC) retention time. The expectation value was determined as the probability assigned by the Protein Prospector search engine that the peptide sequence could be assigned randomly. For each peptide, the time-point $^{15}$N incorporation measurement was determined. The lag time (t0) and the accumulation rate (k0) are fitting parameters used to calculate an exponential accumulation curve described by the time-points. In this study, we did not discriminate between peptides for which no turnover was measured (i.e., a turnover rate slower than 0.001 day$^{-1}$) and peptides that were not observed at later time-points. We relied on the similarity analysis between peptides belonging to the same protein to distinguish between the two cases.

Only peptides assigned with a greater than 95% confidence in a Protein Prospector reverse database search (25) were used in subsequent analysis. For samples collected at later time-points, $^{15}$N-labeled peptides were identified based on (i) molecular weight region of the gel; (ii) the expected LC retention time as observed in the 0 d sample; and (iii) expected mass distribution based on the MW of the peptide, natural isotopic distribution of C, O, S, and H atoms, and $^{14}$N/$^{15}$N ratio ranging from 0.0037 to 0.995 (the natural and algal abundance of $^{15}$N, respectively). For 4,619 brain peptides, 7,226 liver peptides and 1,968 blood peptides, we were able to identify and quantify the mass distribution at all 9 time-points with high statistical confidence as shown in Table 1 below.

TABLE 1

Numbers of peptides and proteins analyzed in this study.

|  | Brain | Liver | Blood |
|---|---|---|---|
| Detected peptides (0 Day) | 14,971 | 14,653 | 4,670 |
| Peptides utilized in protein analysis* | 4,619 | 7,226 | 1,968 |
| Total proteins analyzed | 1,010 | 1,122 | 334 |
| 1 peptide† | 379 | 313 | 107 |
| 2-4 peptides† | 353 | 343 | 111 |
| 5-10 peptides† | 165 | 244 | 71 |
| >10 peptides† | 113 | 222 | 45 |
| Unique proteins (total) |  | 1716 |  |

*Only peptides detected in all 9 time-points were used for protein analysis.
†Number of proteins for which the stated number of peptides were analyzed and averaged.

Figure 4:
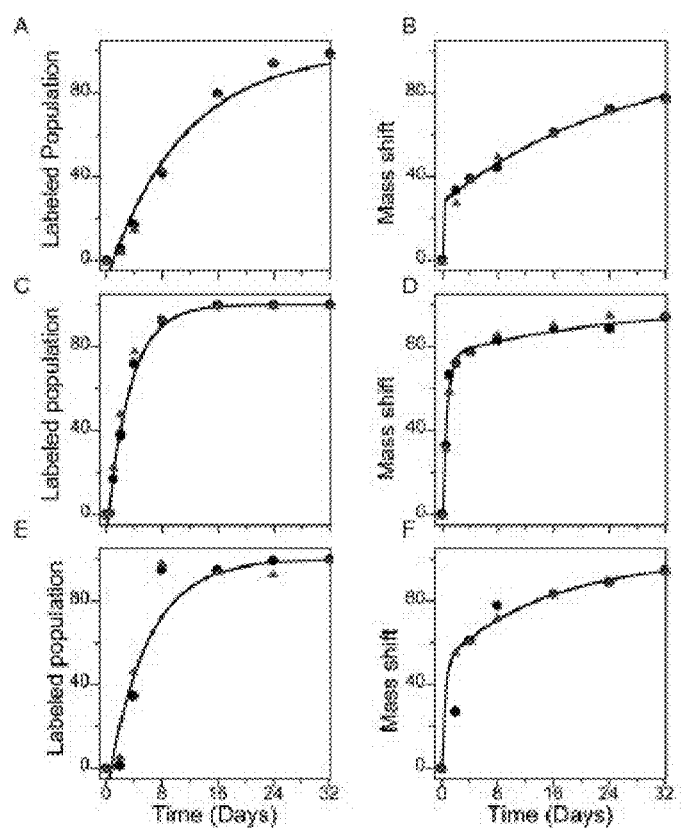
FIG. 4 includes the three graphs of FIG. 4A and three graphs of FIG. 4B showing biological replicates of mass shift and label population measurements. The circles and the triangles indicate two different mice measured at different points in time. Comparisons of the labeled populations (A, C and E) and mass shift (B, D and F) in the brain (A and B), liver (C and D) and blood (E and F) shows that the rate of labeling are very similar between different mice.

Data obtained from duplicate animals at any given time-point showed minimal variation (FIGS. 4A, B, C, D, E and F).

As an example of a typical kinetic labeling pattern, the time-dependent mass increase of the brain-derived Cofilin-1 peptide (NIILEEGKEILVGDVGQTVDDPYTTFVK) is shown in FIG. 1C. Two independent parameters of $^{15}N$ incorporation are evident. First, there is a time-dependent increase in the fraction of the area of the peptide peaks that fall outside the expected unlabelled mass distribution (0 d). Second, the centroid mass of the labeled population (FIG. 1C, arrowheads) increases over time. We refer to these two measurements, normalized to the ratio of unlabelled to fully labeled samples, as "labeled population" and "mass shift," respectively. For the Cofilin-1 peptide, a $^{15}N$-labeled population is clearly visible in samples obtained after 1 day of labeling (FIG. 1C). The labeled protein population is well resolved from the natural isotopic distribution even at the earliest time point, negating the need for the deconvolution of the natural and isotopic mass distributions.

Plots of the labeled population and mass shift for Cofilin-1 and several other peptides are shown in the six graphs of FIGS. 2A and 2B. A number of kinetic trends are evident in the data. First, the increase in mass shift is biphasic, with a rapid initial burst followed by an extended (slow) phase. Second, mass shift kinetics are similar among peptides extracted from the same tissue but different between the three analyzed tissues. Specifically, in the brain, the initial fast phase has a lower amplitude and the second phase has a slower rate in comparison to liver and blood. Third, labeled population has an initial lag phase of ~1 day, followed by a single exponential increase. And lastly, the kinetics of labeled population is highly variable among the analyzed peptides.

Calculating Protein Turnover

Historically, various simplified models have been used to interpret the kinetics of protein turnover in tracer labeling experiments (26-28). These models attempt to reconcile the observed kinetic trends of label uptake with reaction mechanisms consisting of kinetic influx and efflux of theoretical pools of amino acids and proteins (17, 26). Here, we utilize a three-pool model (FIG. 1B) to explain the observed kinetic trends (exemplified by the Coffilin-1 peptide in FIG. 1C and the peptides plotted in FIG. 2).

The global (organism-wide) pool of amino acids can be supplied by two sources: external diet and internal metabolism/catabolism. The global pool provides amino acids for local (tissue-wide) pools used in protein synthesis Amino acids can exit the system (excreted) from the global pool. According to this model, the labeled population in our studies represents the fraction of the protein pool that has turned over at a given time and mass shift of the labeled population reflects the enrichment of the labile nitrogen in the local amino acid pool. The extent of mass shift is a characteristic of the tissue of origin and not a feature of any individual protein. Conversely, the kinetics of labeled population represent the turnover rates of peptides and as such are expected to be highly variable. After a lag period, the labeled population increases exponentially. Fitting this phase to a single exponential equation allows the measurement of the rate of peptide turnover.

Figure 5:
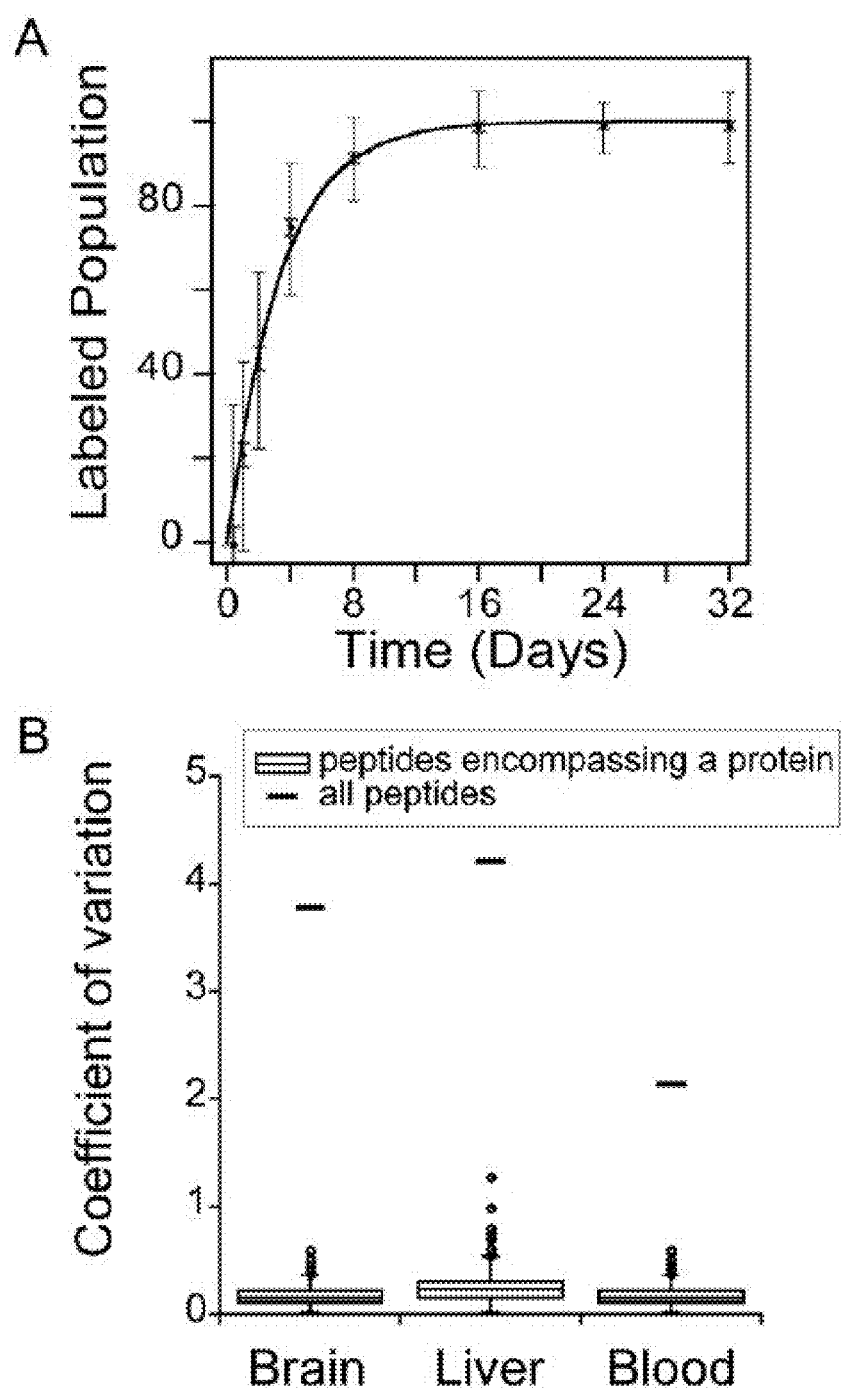
FIG. 5 includes graphs 5A and 5B showing determination of protein turnover rates.

Most proteins in our dataset were represented by more than one peptide. The variability in turnover kinetics among peptides encompassing a single protein was quite low, with the typical coefficient of variation of ~0.25 (FIGS. 5A and 5B). Peptides belonging to a single protein and having similar kinetic profiles of labeled population were averaged to obtain labeled population curves for each protein. Outliers, defined as peptides with Pearson correlations less than 0.9 with respect to the protein average, were excluded. The averaged protein curves were fit to a single exponential equation and the turnover rate for each protein was measured, as shown for blood-extracted serum albumin (FIGS. 6A and 6B).

The measured rates of turnover spanned four orders of magnitude, from 0.002 $d^{-1}$ to 10 $d^{-1}$. In the brain proteins had longer turnover times whereas the distributions of the blood and liver proteins were skewed towards faster turnover rates (FIGS. 6A and 6B). The median turnover rate for the brain peptides was 0.075 $d^{-1}$ compared to 0.23 and 0.20 $d^{-1}$, respectively, for the blood and liver proteins. Thus, the average lifetimes of proteins in the brain, liver, and blood are 9.0, 3.0, and 3.5 d, respectively.

Figure 6:
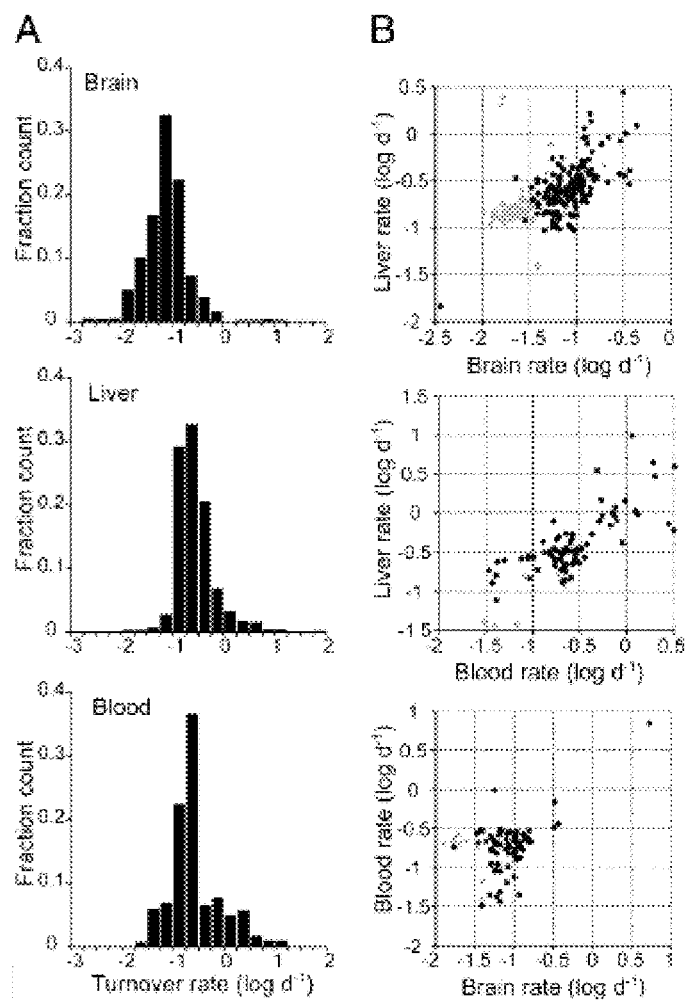
FIG. 6 includes the three bar graphs of 6A and three dot graphs of 6B showing distribution and comparison of protein turnover rates in the brain, liver and blood. 6A shows the distribution of turnover rates. In the brain, proteins have longer turnover times whereas the distribution of the blood and liver proteins were skewed towards faster turnover rates. In 6B a comparison of turnover rates between tissues is shown where the gray dots represent mitochondrial proteins.
Figure 8:
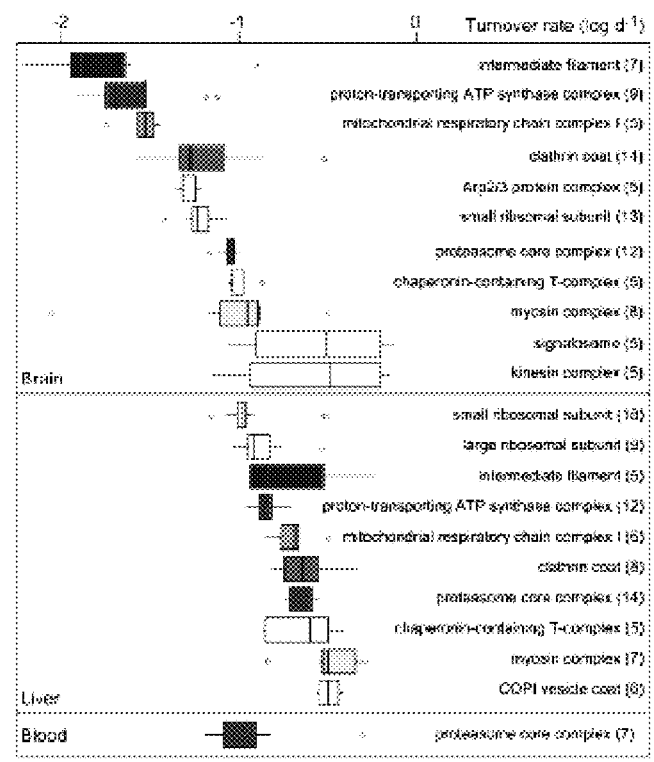
FIG. 8 shows the turnover rates of analyzed subunit proteins that comprise multiprotein complexes. Boxes show the distribution of turnover rates and proteins that participate in multiprotein complexes. The error bar represents the entire range of rates and the dots represent outliers. The numbers in parentheses indicate the number of proteins subunits analyzed and represented in the distribution. Complexes observed in multiple tissues share the same box. White box indicates the complex was detected only in that tissue.
Figure 9:
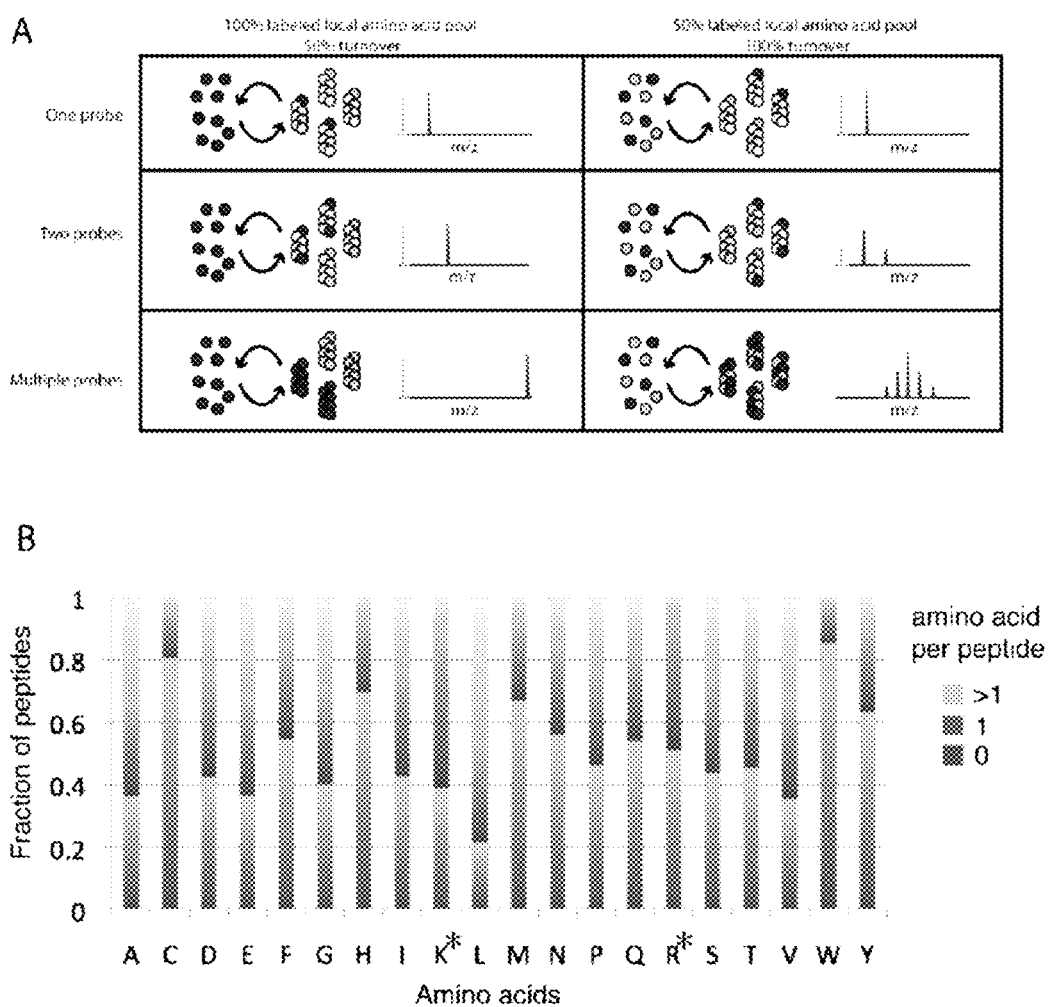
FIG. 9 includes a schematic of FIGS. 9A and 9B showing utilization of ubiquitously labeled feed in enabling the deconvolution of an amino acid labeling pool versus protein turnover.

Many of the proteins uniquely expressed in the brain had slow rates of turnover. For example, myelin basic protein, an abundant constituent of the myelin sheath, had a half life of up to a year. Furthermore, proteins present in all three tissues showed longer turnover times in the brain (FIGS. 6-8). In particular, mitochondrial proteins (FIG. 6B) tend to have a much slower turnover rate in the brain in comparison to the liver and blood.

Correlation of Turnover Rates to Function

We next sought to uncover statistically significant correlations between turnover rates and other biological properties of the proteins kinetically analyzed in our studies. We created a list of gene ontology (GO) terms (30) associated with the proteins in blood, liver, and brain, then separated the proteins into bins according to turnover rates, ranging from −3 to 2 log $d^{-1}$ and overlapping by 0.5 log $d^{-1}$ at intervals of 0.25 log $d^{-1}$. The relative prevalence of GO terms in each rate bin was calculated as the ratio between the number of observed proteins belonging to the GO term in that bin to the number expected by random chance. The statistical significance of the enrichment was determined by calculating the Fisher exact-test p-value (31). We identified 330 GO terms that were enriched in one or more rate bins with a statistical significance of p<0.001, which included 108 terms for brain, 124 for liver, and 98 for blood (FIG. 7). Multiple GO terms can be related to one another in a hierarchical fashion (30). Thus, the same group of genes can cause the enrichment of multiple, related GO terms. To negate this redundancy, GO terms that were represented by overlapping groups of proteins in the data (overlap of 30% or more) were grouped into empirically named clusters. The bin enrichments for each cluster were determined by averaging the enrichments for each of the constituent GO terms.

Secreted proteins (apolipoprotein, chylomicron, complement factors) and proteins involved in signaling and protein folding (e.g., chaperones) have the fastest rates of turnover. We measured half-lives of 2-10 h for these proteins. Proteins contained in the nucleosome (e.g., histones) and those involved in the maintenance of the myelin sheath showed the longest turnover rates, with measured half-lives of up to 1 year. Different proteins associated with an organelle turn over at similar rates. For example, mitochondrial proteins generally showed long half-lives, and most proteins residing in the ER had half-lives of 6-10 days (FIG. 7). It should be noted that FIG. 7 is not an exhaustive list of functional categories that are enriched for proteins with specific half-lives. FIG. 7 is limited to functional categories that were represented by a sufficient number of proteins in our dataset to enable the measurement of enrichments with a high degree of statistical confidence ($p<0.001$).

Turnover of Protein Complex Subunits

GO annotations were used to identify proteins in the dataset belonging to multiprotein complexes, excluding highly heterogeneous protein complexes (e.g., microtubule, nucleosome, etc.) We identified complexes that contained ≥5 protein subunits in our dataset and plotted the distribution of their turnover rates (FIG. 8). The proteins contained within each complex and their respective turnover rates were obtained. Without exception, all protein complexes identified in both brain and liver turned over more slowly in the brain than in the liver. For example, 12 subunits of the proteasome were identified in both the brain and the liver. The average half-life for the observed subunits in the brain was 8 d, while the average half-life for subunits in the liver was 4 days. The half-lives among subunits of the proteasome were similar, with a standard deviation of only 1.3 d in the brain. The subunits of many large, abundant complexes such as ATP synthase and the ribosome have similarly narrow ranges of turnover rates.

REFERENCES

1. Goldberg A L & St John A C (1976) Intracellular protein degradation in mammalian and bacterial cells: Part 2. Annu. Rev. Biochem. 45:747-803.
2. Mortimore G E, Poso A R, & Lardeux B R (1989) Mechanism and regulation of protein degradation in liver. Diabetes Metab. Rev. 5:49-70.
3. Rousset S, et al. (2007) UCP2 is a mitochondrial transporter with an unusual very short half-life. FEBS Lett. 581:479-482.
4. Verzijl N, et al. (2000) Effect of collagen turnover on the accumulation of advanced glycation end products. J. Biol. Chem. 275:39027-39031.
5. Ivan M, et al. (2001) HIFalpha targeted for VHL-mediated destruction by proline hydroxylation: implications for O2 sensing. Science 292:464-468.
6. Jaakkola P, et al. (2001) Targeting of HIF-alpha to the von Hippel-Lindau ubiquitylation complex by O2-regulated prolyl hydroxylation. Science 292:468-472.
7. Pratt J M, et al. (2002) Dynamics of protein turnover, a missing dimension in proteomics. Mol. Cell. Proteomics 1:579-591.
8. Hellerstein M K (2004) New stable isotope-mass spectrometric techniques for measuring fluxes through intact metabolic pathways in mammalian systems: introduction of moving pictures into functional genomics and biochemical phenotyping. Metab. Eng. 6:85-100.
9. van Remmen H, Ward W F, Sabia R V, & Richardson A (1995) Gene expression and protein degradation [in aging]. Handbook of Physiology Section 11: Aging, ed Masoro E J (American Physiological Society by Oxford University Press, New York), pp 171-234.
10. Sun F, et al. (2006) Derlin-1 promotes the efficient degradation of the cystic fibrosis transmembrane conductance regulator (CFTR) and CFTR folding mutants. J. Biol. Chem. 281:36856-36863.
11. Martinez-Vicente M, Sovak G, & Cuervo A M (2005) Protein degradation and aging. Exp. Gerontol. 40:622-633.
12. Bachmair A, Finley D, & Varshavsky A (1986) In vivo half-life of a protein is a function of its amino-terminal residue. Science 234:179-186.
13. Dice J F & Goldberg A L (1975) A statistical analysis of the relationship between degradative rates and molecular weights of proteins. Arch. Biochem. Biophys. 170:213-219.
14. Dice J F & Goldberg A L (1975) Relationship between in vivo degradative rates and isoelectric points of proteins. Proc. Natl. Acad. Sci. USA 72:3893-3897.
15. Tompa P, Prilusky J, Silman I, & Sussman J L (2008) Structural disorder serves as a weak signal for intracellular protein degradation. Proteins 71:903-909.
16. Buchanan D L (1961) Total carbon turnover measured by feeding a uniformly labeled diet. Arch. Biochem. Biophys. 94:500-511.
17. Garfinkel D & Lajtha A (1963) A metabolic inhomogeneity of glycine in vivo. I. Experimental determination. J. Biol. Chem. 238:2429-2434.
18. Lajtha A (1959) Amino acid and protein metabolism of the brain. V. Turnover of leucine in mouse tissues. J. Neurochem. 3:358-365.
19. Lajtha A, Berl S, & Waelsch H (1959) Amino acid and protein metabolism of the brain. IV. The metabolism of glutamic acid. J. Neurochem. 3:322-332.
20. Nikolov E N, Dineva B B, Dabeva M D, & Nikolov T K (1987) Turnover of ribosomal proteins in regenerating rat liver after partial hepatectomy. Int. J. Biochem. 19:159-163.
21. McClatchy D B, Dong M Q, Wu C C, Venable J D, & Yates J R, 3rd (2007) 15N metabolic labeling of mammalian tissue with slow protein turnover. J. Proteome Res. 6:2005-2010.
22. Doherty M K, Hammond D E, Clague M J, Gaskell S J, & Beynon R J (2009) Turnover of the human proteome: determination of protein intracellular stability by dynamic SILAC. J. Proteome Res. 8:104-112.
23. Wu C C, MacCoss M J, Howell K E, Matthews D E, & Yates J R, 3rd (2004) Metabolic labeling of mammalian organisms with stable isotopes for quantitative proteomic analysis. Anal. Chem. 76:4951-4959.
24. Salazar M, Martinez E, Madrigal E, Ruiz L E, & Chamorro G A (1998) Subchronic toxicity study in mice fed *Spirulina* maxima. J. Ethnopharmacol. 62:235-241.
25. Chalkley R J, et al. (2005) Comprehensive analysis of a multidimensional liquid chromatography mass spectrometry dataset acquired on a quadrupole selecting, quadrupole collision cell, time-of-flight mass spectrometer: II. New developments in Protein Prospector allow for reliable and comprehensive automatic analysis of large datasets. Mol. Cell. Proteomics 4:1194-1204.

26. Garfinkel D (1963) A metabolic inhomogeneity of glycine in vivo. II. Computer simulation. J. Biol. Chem. 238:2435-2439.
27. Schimke R T (1970) Regulation of protein degradation in mammalian tissues. Mammalian Protein Metabolism, eds Munro H N & Allison J B (Academic Press, Inc., New York), Vol 4, pp 177-228.
28. Waterlow J C, Garlick P J, & Millward D J (1978) Protein turnover in mammalian tissues and in the whole body (North-Holland Publishing Co., New York).
29. Taylor K B (2002) Enzyme kinetics and mechanisms (Kluwer Academic, Boston) p 227.
30. The Gene Ontology Consortium (2008) The Gene Ontology project in 2008. Nucleic Acids Res. 36:D440-D444.
31. Fisher R A (1922) On the interpretation of x 2 from J. R. Stat. Soc. 85:87-94.
32. Mao L M, et al. (2009) Stability of surface NMDA receptors controls synaptic and behavioral adaptations to amphetamine. Nat. Neurosci. 12:602-610.
33. Schwartz J H (2003) Ubiquitination, protein turnover, and long-term synaptic plasticity. Sci. STKE 2003:pe26.
34. Kruger M, et al. (2008) SILAC mouse for quantitative proteomics uncovers kindlin-3 as an essential factor for red blood cell function. Cell 134:353-364.
35. Ong S-E & Mann M (2006) A practical recipe for stable isotope labeling by amino acids in cell culture (SILAC). Nat. Protoc. 1:2650-2660.
36. Doherty M K, Whitehead C, McCormack H, Gaskell S J, & Beynon R J (2005) Proteome dynamics in complex organisms: using stable isotopes to monitor individual protein turnover rates. Proteomics 5:522-533.
37. Ishihama Y, et al. (2005) Exponentially modified protein abundance index (emPAI) for estimation of absolute protein amount in proteomics by the number of sequenced peptides per protein. Mol. Cell. Proteomics 4:1265-1272.
38. Wang Z, O'Connor T P, Heshka S, & Heymsfield S B (2001) The reconstruction of Kleiber's law at the organ-tissue level. J. Nutr. 131:2967-2970.
39. Tal R, Winter G, Ecker N, Klionsky D J, & Abeliovich H (2007) Aup1p, a yeast mitochondrial protein phosphatase homolog, is required for efficient stationary phase mitophagy and cell survival. J. Biol. Chem. 282:5617-5624.
40. Journo D, Mor A, & Abeliovich H (2009) Aup1-mediated regulation of Rtg3 during mitophagy. J. Biol. Chem. 284:35885-35895.
41. Drews O, et al. (2007) Mammalian proteasome subpopulations with distinct molecular compositions and proteolytic activities. Mol. Cell. Proteomics 6:2021-2031.
42. Wei N & Deng X W (2003) The COP9 signalosome. Annu. Rev. Cell Dev. Biol. 19:261-286.
43. Tomoda K, et al. (2002) The cytoplasmic shuttling and subsequent degradation of p27Kip1 mediated by Jab1/CSN5 and the COP9 signalosome complex. J. Biol. Chem. 277:2302-2310.
44. Prusiner S B (2001) Prions. Fields Virology, eds Knipe D M & Howley P M (Lippincott Williams & Wilkins, Philadelphia), 4th Ed, pp 3063-3087.
45. Dobson C M (1999) Protein misfolding, evolution and disease. Trends Biochem. Sci. 24:329-332.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method, comprising the steps of:
   feeding to a subject a composition comprised of a plurality of isotopically labeled amino acids labeled with a $^{15}N$ isotope wherein the administering is carried out by feeding the composition to a subject over a period of days;
   allowing the $^{15}N$ labeled amino acids to incorporate into proteins of the subject;
   harvesting tissue samples from the subject at different points in time over a period of days at intervals of every day or longer; and analyzing the harvested tissue samples and determining a level of $^{15}$N isotope present; wherein the composition administered to the subject is $^{15}$N-enriched blue-green algae (*Spirulina plantenis*).

2. The method of claim 1, wherein the analyzing comprises:
separating proteins based on a physical characteristic of the proteins; and
subjecting proteins of a given size to mass spectroscopy and detecting an $^{15}$N isotope of the $^{15}$N labeled amino acids.

3. The method of claim 2, wherein the physical characteristic is selected from the group consisting of protein size, protein shape, protein size and shape combined and isoelectric point.

4. The method of claim 2, wherein the labeled amino acids are allowed to incorporate into a plurality of different proteins in the subject, and the analyzing comprise tracking different proteins in different tissues of the subject.

5. The method of claim 1, wherein the analyzing further comprises tracking a single protein in multiple different tissues of the subject.

6. The method of claim 1, wherein the analyzing comprises determining a ratio of $^{15}$N isotope present in a first type of tissue relative to a second type of tissue.

7. The method of claim 2, wherein the subject is a mouse.

8. The method of claim 1, wherein the subject is a human and the tissue samples harvested are blood samples.

9. The method of claim 1, wherein the analyzing comprises:
separating proteins based on protein size or other physical characteristic, such including but not limited to isoelectric point; and
subjecting proteins of a given size to mass spectrometry for determination of the amount and pattern of $^{15}$N isotopic labeling in said proteins.

10. The method of claim 1, wherein the proteins isolated are subjected to partial proteolytic degradation, with an enzyme such as trypsin; and peptide fragments of said proteolytic digestion are subjected to mass spectrometry for determination of the amount and pattern of $^{15}$N isotopic labeling in said peptides.

11. A method of testing affects of a drug on protein turnover, comprising the steps of:
feeding a group of substantially identical test animals a composition comprised of a plurality of isotopically labeled amino acids labeled with a $^{15}$N wherein the administering is carried out by feeding the composition to a subject over a period of days;
dividing the test animals into a first group and a second group:
administering a drug to the first group, while not administering the drug to the second group;
allowing the labeled amino acids to incorporate into proteins of the animals in the first group and the second group;
harvesting tissue samples from animals of the first group and the second group over a period of days at intervals of every day or longer;
analyzing tissue samples from the first group and the second group and determining a level of isotope $^{15}$N in the tissue samples; and
comparing the level of $^{15}$N isotope in the samples from the first group with the level of $^{15}$N isotope in the samples of the second group in order to determine an affect on protein turnover caused by the drug;
wherein the composition administered to the subject is $^{15}$N-enriched blue-green algae (*Spirulina plantenis*).

12. The method of claim 11, wherein the first group of test animals and the second group of test animals each comprise two or more animals, and further wherein tissue is harvested from each group of animals at two or more different points in time.

13. The method of claim 11, wherein the test animals are mice.

14. The method of claim 11, wherein the analyzing comprises:
separating proteins based on protein size; and
subjecting proteins of a given size to mass spectroscopy and detecting an $^{15}$N isotope of the $^{15}$N labeled amino acids.

15. The method of claim 11, wherein the analyzing comprises:
separating proteins based on protein size or other physical characteristic, such including but not limited to isoelectric point; and
subjecting proteins of a given size to mass spectrometry for determination of the amount and pattern of $^{15}$N isotopic labeling in said proteins.

16. The method of claim 11, wherein the proteins isolated are subjected to partial proteolytic degradation, with an enzyme such as trypsin; and peptide fragments of said proteolytic digestion are subjected to mass spectrometry for determination of the amount and pattern of $^{15}$N isotopic labeling in said peptides.

17. A method, comprising the steps of:
feeding to a mouse a composition comprised of a plurality of isotopically labeled amino acids labeled with a $^{15}$N isotope wherein the administering is carried out by feeding the composition to a mouse over a period of days;
allowing the $^{15}$N labeled amino acids to incorporate into proteins of the mouse;
harvesting tissue samples from the mouse at different points in time over a period of days at intervals of every day or longer; and
analyzing the harvested tissue samples and determining a level of $^{15}$N isotope present;
wherein the composition administered to the mouse is $^{15}$N-enriched blue-green algae (*Spirulina plantenis*);
separating proteins based on protein size; and
subjecting proteins of a given size to mass spectroscopy and detecting an $^{15}$N isotope,
wherein the analyzing further comprises tracking a single protein in multiple different tissues of the subject, and
wherein the analyzing comprises determining a ratio of $^{15}$N isotope present in a first type of tissue relative to a second type of tissue.

* * * * *

SEQUENCE LISTING

```
<160> NUMBER OF SEQ ID NOS: 1

<210> SEQ ID NO 1
<211> LENGTH: 28
<212> TYPE: PRT
<213> ORGANISM: Artificial Sequence
<220> FEATURE:
<223> OTHER INFORMATION: synthetic peptide

<400> SEQUENCE: 1

Asn Ile Ile Leu Glu Glu Gly Lys Glu Ile Leu Val Gly Asp Val Gly
1               5                   10                  15

Gln Thr Val Asp Asp Pro Tyr Thr Thr Phe Val Lys
            20                  25
```